(12) United States Patent
Noda et al.

(10) Patent No.: US 7,278,984 B2
(45) Date of Patent: Oct. 9, 2007

(54) SYSTEM AND METHOD FOR CONTROLLING RATE OF HEAT EXCHANGE WITH PATIENT

(75) Inventors: Wayne A. Noda, Mission Viejo, CA (US); Scott M. Evans, Santa Ana, CA (US); Mark Evan Whitebook, Capistrano Beach, CA (US); David P. Balding, Mission Viejo, CA (US)

(73) Assignee: Alsius Corporation, Irvine, CA (US)

( * ) Notice: Subject to any disclaimer, the term of this patent is extended or adjusted under 35 U.S.C. 154(b) by 140 days.

(21) Appl. No.: 10/334,414

(22) Filed: Dec. 31, 2002

(65) Prior Publication Data

US 2004/0127851 A1  Jul. 1, 2004

(51) Int. Cl.
*A61F 7/12* (2006.01)

(52) U.S. Cl. ....................... 604/113; 604/500

(58) Field of Classification Search ............... 604/113, 604/114, 27, 28, 43, 500; 137/340, 334, 137/341; 165/177–184
See application file for complete search history.

(56) References Cited

U.S. PATENT DOCUMENTS

| | | | |
|---|---|---|---|
| 2,058,780 A | 10/1936 | Elliott |
| 2,077,453 A | 4/1937 | Albright |
| 2,190,384 A | 2/1940 | Newman |
| 2,308,484 A | 1/1943 | Auzin et al. |
| 3,125,096 A | 3/1964 | Antiles et al. |
| 3,142,158 A | 7/1964 | Podolsky |
| 3,238,944 A | 3/1966 | Hirschhorn |
| 3,282,267 A | 11/1966 | Eidus |
| 3,327,713 A | 6/1967 | Eidus |
| 3,425,419 A | 2/1969 | Dato |
| 3,460,538 A | 8/1969 | Armstrong |
| 3,504,674 A | 4/1970 | Swenson et al. |
| 3,738,372 A | 6/1973 | Shioshvili |
| 3,776,241 A | 12/1973 | Magilton et al. |
| 3,897,790 A | 8/1975 | Magilton et al. |
| 3,913,581 A | 10/1975 | Ritson et al. |
| 4,010,795 A | 3/1977 | Stenberg |
| 4,014,317 A | 3/1977 | Bruno |

(Continued)

FOREIGN PATENT DOCUMENTS

EP        0 524 662        1/1993

(Continued)

OTHER PUBLICATIONS

DeWitt, Douglas, et al., *Accurate measurement of brain temperature*, Crit Care Med 1998 vol. 26, No. 3, pp. 431-432.

(Continued)

*Primary Examiner*—Catherine S. Williams
(74) *Attorney, Agent, or Firm*—Buchanan Ingersoll & Rooney LLP

(57) ABSTRACT

A patient control system uses a patient-implanted catheter in thermal communication with a fluid bath via a circulating fluid circuit. A controller automatically controls the temperature of the fluid bath as required for selectively cooling or heating the patient in accordance with patient temperature measurements. The controller thermally decouples the catheter and patient from the fluid bath during changes in fluid bath temperatures in order to overcome the effects of system thermal mass.

24 Claims, 2 Drawing Sheets

U.S. PATENT DOCUMENTS

| | | |
|---|---|---|
| 4,111,209 A | 9/1978 | Wolvek et al. |
| 4,154,245 A | 5/1979 | Daily |
| 4,181,132 A | 1/1980 | Parks |
| 4,197,667 A | 4/1980 | Helfenstine et al. |
| 4,249,923 A | 2/1981 | Walda |
| 4,298,006 A | 11/1981 | Parks |
| 4,305,388 A | 12/1981 | Brisson |
| 4,312,364 A | 1/1982 | Convert et al. |
| 4,416,280 A | 11/1983 | Carpenter et al. |
| 4,416,281 A | 11/1983 | Cooper et al. |
| 4,445,886 A | 5/1984 | Osterholm |
| 4,497,324 A | 2/1985 | Sullivan et al. |
| 4,546,759 A | 10/1985 | Solar |
| 4,583,969 A | 4/1986 | Mortensen |
| 4,632,125 A | 12/1986 | Webler et al. |
| 4,638,436 A | 1/1987 | Badger et al. |
| 4,639,353 A | 1/1987 | Takemura et al. |
| 4,662,383 A | 5/1987 | Sogawa et al. |
| 4,672,962 A | 6/1987 | Hershenson |
| 4,682,978 A | 7/1987 | Martin |
| 4,686,085 A | 8/1987 | Osterholm |
| 4,736,748 A | 4/1988 | Nakamura et al. |
| 4,745,922 A | 5/1988 | Taylor |
| 4,747,826 A | 5/1988 | Sassano |
| 4,748,979 A | 6/1988 | Hershenson |
| 4,750,493 A | 6/1988 | Brader |
| 4,754,752 A | 7/1988 | Ginsburg et al. |
| 4,759,349 A | 7/1988 | Betz et al. |
| 4,791,930 A | 12/1988 | Suzuki et al. |
| 4,796,640 A | 1/1989 | Webler |
| 4,804,358 A | 2/1989 | Karcher et al. |
| 4,813,210 A | 3/1989 | Masuda et al. |
| 4,819,655 A | 4/1989 | Webler |
| 4,823,076 A | 4/1989 | Haines et al. |
| 4,841,981 A | 6/1989 | Tanabe et al. |
| RE32,983 E | 7/1989 | Levy |
| 4,844,074 A | 7/1989 | Kurucz |
| 4,850,958 A | 7/1989 | Berry et al. |
| 4,850,969 A | 7/1989 | Jackson |
| 4,860,744 A | 8/1989 | Johnson et al. |
| 4,883,455 A | 11/1989 | Leonard |
| 4,899,741 A | 2/1990 | Bentley et al. |
| 4,901,734 A | 2/1990 | Griffin et al. |
| 4,907,589 A | 3/1990 | Cosman |
| 4,911,689 A | 3/1990 | Hattler |
| 4,917,667 A | 4/1990 | Jackson |
| 4,920,963 A | 5/1990 | Brader |
| 4,941,475 A | 7/1990 | Williams et al. |
| 4,955,377 A | 9/1990 | Lennox et al. |
| 4,975,247 A | 12/1990 | Badolato et al. |
| 4,986,809 A | 1/1991 | Hattler |
| 4,987,896 A | 1/1991 | Hakamatsu |
| RE33,561 E | 3/1991 | Levy |
| 5,004,456 A | 4/1991 | Botterbusch et al. |
| 5,004,461 A | 4/1991 | Wilson |
| 5,011,468 A | 4/1991 | Lundquist et al. |
| 5,019,075 A | 5/1991 | Spears et al. |
| 5,021,045 A | 6/1991 | Buckberg et al. |
| 5,037,383 A | 8/1991 | Vaslef et al. |
| 5,041,089 A | 8/1991 | Mueller et al. |
| 5,059,167 A | 10/1991 | Lundquist et al. |
| 5,066,578 A | 11/1991 | Wikman-Coffelt |
| 5,078,713 A | 1/1992 | Varney |
| 5,092,841 A | 3/1992 | Spears |
| 5,098,376 A | 3/1992 | Berry et al. |
| 5,106,360 A | 4/1992 | Ishiwara et al. |
| 5,122,113 A | 6/1992 | Hattler |
| 5,139,496 A | 8/1992 | Hed |
| 5,147,355 A | 9/1992 | Friedman et al. |
| 5,147,385 A | 9/1992 | Beck et al. |
| 5,151,100 A | 9/1992 | Abele et al. |
| 5,158,534 A | 10/1992 | Berry et al. |
| 5,167,960 A | 12/1992 | Ito et al. |
| 5,174,285 A | 12/1992 | Fontenot |
| 5,182,317 A | 1/1993 | Winters et al. |
| 5,191,883 A | 3/1993 | Lennox et al. |
| 5,196,024 A | 3/1993 | Barath |
| 5,207,640 A | 5/1993 | Hattler |
| 5,211,631 A | 5/1993 | Sheaff |
| 5,221,270 A | 6/1993 | Parker |
| 5,230,862 A | 7/1993 | Berry et al. |
| 5,248,312 A | 9/1993 | Langberg |
| 5,250,070 A | 10/1993 | Parodi |
| 5,257,977 A | 11/1993 | Eshel |
| 5,259,839 A | 11/1993 | Burns |
| 5,261,399 A | 11/1993 | Klatz et al. |
| 5,261,411 A | 11/1993 | Hughes |
| 5,262,451 A | 11/1993 | Winters et al. |
| 5,269,758 A | 12/1993 | Taheri |
| 5,271,410 A | 12/1993 | Wolzinger et al. |
| 5,271,743 A | 12/1993 | Hattler |
| 5,275,595 A | 1/1994 | Dobak, III |
| 5,279,598 A | 1/1994 | Sheaff |
| 5,281,213 A | 1/1994 | Milder et al. |
| 5,281,215 A | 1/1994 | Milder |
| 5,304,214 A | 4/1994 | DeFord et al. |
| 5,324,260 A | 6/1994 | O'Neill et al. |
| 5,324,286 A | 6/1994 | Fowle |
| 5,338,770 A | 8/1994 | Winters et al. |
| 5,342,301 A | 8/1994 | Saab |
| 5,342,693 A | 8/1994 | Winters et al. |
| 5,346,508 A | 9/1994 | Hastings |
| 5,348,554 A | 9/1994 | Imran et al. |
| 5,354,277 A | 10/1994 | Guzman et al. |
| 5,370,616 A | 12/1994 | Keith et al. |
| 5,382,234 A | 1/1995 | Cornelius et al. |
| 5,385,540 A | 1/1995 | Abbott et al. |
| 5,405,322 A | 4/1995 | Lennox et al. |
| 5,411,477 A | 5/1995 | Saab |
| 5,423,744 A | 6/1995 | Gencheff et al. |
| 5,423,807 A | 6/1995 | Milder |
| 5,433,740 A | 7/1995 | Yamaguchi |
| 5,437,637 A | 8/1995 | Lieber et al. |
| 5,437,673 A | 8/1995 | Baust et al. |
| 5,451,208 A | 9/1995 | Goldrath |
| 5,452,582 A | 9/1995 | Longsworth |
| 5,478,309 A | 12/1995 | Sweezer et al. |
| 5,486,204 A | 1/1996 | Clifton |
| 5,486,208 A | 1/1996 | Ginsburg |
| 5,501,663 A | 3/1996 | Hattler et al. |
| 5,531,776 A | 7/1996 | Ward et al. |
| 5,545,134 A | 8/1996 | Hilaire et al. |
| 5,545,137 A | 8/1996 | Rudie et al. |
| 5,545,161 A | 8/1996 | Imran |
| 5,549,552 A | 8/1996 | Peters et al. |
| 5,549,559 A | 8/1996 | Eshel |
| 5,562,606 A | 10/1996 | Huybregts |
| 5,563,584 A | 10/1996 | Rader et al. |
| 5,588,965 A | 12/1996 | Burton et al. |
| 5,595,181 A | 1/1997 | Hubbard |
| 5,596,995 A | 1/1997 | Sherman et al. |
| 5,599,307 A | 2/1997 | Bacher et al. |
| 5,607,463 A | 3/1997 | Schwartz et al. |
| 5,609,591 A | 3/1997 | Daikuzono |
| 5,609,620 A | 3/1997 | Daily |
| 5,624,392 A | 4/1997 | Saab |
| 5,634,720 A | 6/1997 | Gallup et al. |
| 5,655,548 A | 8/1997 | Nelson et al. |
| 5,656,420 A | 8/1997 | Chien |
| 5,693,080 A | 12/1997 | Wallsten et al. |
| 5,702,358 A | 12/1997 | Witherspoon et al. |
| 5,702,435 A | 12/1997 | Maytal |
| 5,716,386 A | 2/1998 | Ward et al. |
| 5,733,319 A | 3/1998 | Neilson et al. |

| | | |
|---|---|---|
| 5,735,809 A | 4/1998 | Gorsuch |
| 5,755,756 A | 5/1998 | Freedman, Jr. et al. |
| 5,758,505 A | 6/1998 | Dobak, III et al. |
| 5,759,182 A | 6/1998 | Varney et al. |
| 5,776,176 A | 7/1998 | Rudie |
| 5,787,715 A | 8/1998 | Dobak, III et al. |
| 5,800,375 A | 9/1998 | Sweezer et al. |
| 5,800,486 A | 9/1998 | Thome et al. |
| 5,800,493 A | 9/1998 | Stevens et al. |
| 5,807,342 A | 9/1998 | Musgrave et al. |
| 5,833,624 A | 11/1998 | Rom et al. |
| 5,833,688 A | 11/1998 | Sieben et al. |
| 5,837,003 A | 11/1998 | Ginsburg |
| 5,861,021 A | 1/1999 | Thome et al. |
| 5,865,789 A | 2/1999 | Hattler |
| 5,868,735 A | 2/1999 | Lafontaine |
| 5,879,316 A | 3/1999 | Safar et al. |
| 5,879,329 A | 3/1999 | Ginsburg |
| 5,879,347 A | 3/1999 | Saadat |
| 5,902,299 A | 5/1999 | Jayaraman |
| 5,906,588 A | 5/1999 | Safar et al. |
| 5,975,081 A | 11/1999 | Hood et al. |
| 5,976,103 A | 11/1999 | Martin |
| 5,989,238 A | 11/1999 | Ginsburg |
| 6,042,559 A | 3/2000 | Dobak, III |
| 6,096,068 A | 8/2000 | Dobak, III et al. |
| 6,110,168 A | 8/2000 | Ginsburg |
| 6,126,684 A | 10/2000 | Gobin et al. |
| 6,146,411 A * | 11/2000 | Noda et al. ............... 607/105 |
| 6,149,670 A | 11/2000 | Worthen et al. |
| 6,149,673 A | 11/2000 | Ginsburg |
| 6,149,676 A | 11/2000 | Ginsburg |
| 6,165,017 A | 12/2000 | Kuo |
| 6,231,594 B1 | 5/2001 | Dae |
| 6,264,679 B1 | 7/2001 | Keller et al. |
| 6,287,326 B1 | 9/2001 | Pecor |
| 6,290,717 B1 | 9/2001 | Philips |
| 6,299,599 B1 | 10/2001 | Pham et al. |
| 6,336,911 B1 | 1/2002 | Westerbeck |
| 6,368,304 B1 | 4/2002 | Aliberto et al. |
| 6,405,080 B1 | 6/2002 | Lasersohn et al. |
| 6,432,124 B1 | 8/2002 | Worthen et al. |
| 6,454,792 B1 | 9/2002 | Noda et al. |
| 6,454,793 B1 | 9/2002 | Evans et al. |
| 6,529,775 B2 | 3/2003 | Whitebook et al. |
| 6,572,640 B1 * | 6/2003 | Balding et al. ............. 607/105 |
| 6,581,403 B2 * | 6/2003 | Whitebook et al. ............ 62/434 |
| 6,620,189 B1 * | 9/2003 | Machold et al. ............. 607/106 |
| 2001/0047196 A1 * | 11/2001 | Ginsburg et al. ............. 607/96 |

FOREIGN PATENT DOCUMENTS

| | | |
|---|---|---|
| EP | 0 853 951 | 7/1998 |
| JP | 63283638 | 11/1998 |
| SU | 848031 | 10/1979 |
| WO | WO 84/02839 | 8/1984 |
| WO | WO 91/05528 | 5/1991 |
| WO | WO 92/10227 | 6/1992 |
| WO | WO 98/26831 | 6/1998 |
| WO | WO 98/31312 | 7/1998 |

OTHER PUBLICATIONS

Rumana, Christopher S., et al., *Brain temperature exceeds systemic temperature in head-injured patients*, Crit Care Med 1998 vol. 26, No. 3, pp. 562-567.

Henker, Richard A., et al., *Comparison of brain temperature with bladder and rectal temperatures in adults with severe head injury*, Neurosurgery, vol. 42, No. 5, May 1998.

Maher, John et al., *Hypothermia as a potential treatment for cerebral ischemia*, Cerebrovascular and Brain Metabolism Reviews, 5:277-300, pp. 277-295.

Bruder, Nicolas, MD., et al., *Influence of body temperature, with or without sedation, on energy expenditure in severe head-injured patients*, Crit Care Med 1998 vol. 26, No. 3, pp. 568-572.

Marion, Donald W., et al., *Treatment of traumatic brain injury with moderate hypothermia*, The New England Journal of Medicine, Feb. 20, 1997, pp. 540-546.

Jenkins, Ian et al., *Postbypass Hypothermia and Its Relationship to the Energy Balance of Cardiopulmonary Bypass*, Journal of Cardiotheroacic and Vascular Anesthesia, vol. 5, No. 2 (Apr. 1991), pp. 135-138.

White, Robert J. et al., *Profound Selective Cooling and Ischemia of Primate Brain Without Pump or Oxygenator*, Surgery, Jul. 1969, vol. 66, No. 1, pp. 224-232.

Kaye, William et al., *Improving Outcome from Cardiac Arrest in the Hospital with a Reorganized and Strengthened Chain of Survival: an American View*, Resuscitation 31 (1996) 181-186.

Saadjian, A., et al., *Cardiac Output Measurement by Thermodilution*, Med. Progr. Technol 3, (1976), pp. 161-167.

Teoh, Kevin H., et al., *Accelerated Mycardial Metabolic Recovery with Terminal Warm Blood Cardioplegia*, J Thorac Cardiovasc Surg 91:888-895, 1986.

\* cited by examiner

SYSTEM AND METHOD FOR CONTROLLING RATE OF HEAT EXCHANGE WITH PATIENT

BACKGROUND OF THE INVENTION

The invention relates to patient temperature control in medical applications.

DESCRIPTION OF RELATED ART

Advantages of reduced body temperature for medical treatment are well known. By way of example, it has been found particularly desirable to lower the temperature of body tissue in order to reduce the metabolism of the body. Lowered body temperature also reduces the permeability of the blood/brain barrier, inhibiting release of damaging neurotransmitters, and also inhibits calcium-mediated effects. Lowered body temperature also inhibits brain edema and lowers intracranial pressure.

A systemic approach to reduced body temperature involves a reduction of overall body temperature, for example to realize some of the advantages noted above. This has been particularly desirable in surgical applications where the reduced metabolism has made it possible to more easily accommodate lengthy operative procedures. Systemic body temperature reduction can involve the use of catheters for transferring heat to or from blood flowing within a patient's blood vessel, as disclosed by Ginsburg in U.S. Pat. No. 5,486,208. A closed loop heat exchange catheter is also disclosed by Saab in U.S. 5,486,208. A closed loop heat exchange catheter is also disclosed by Saab in U.S. Pat. No. 5,624,392. A cooling device for whole-body temperature reduction that utilizes the circulatory system of the body is known to be particulary efficient since the entire volume of the body is constantly perfused with the cold fluid at a capillary level.

Alternatively, the temperature of a selected portion of the body of a patient can be reduced without substantially affecting the temperature of the remaining portions of the body or affecting core body temperature. The selected body portion will usually be associated with a body conduit which conveys a body fluid to the selected body portion. Of particular interest are the organs of the body which are commonly nourished and maintained by a flow of blood in the arterial system. For example, a flow of blood is introduced to the brain through the carotid artery. By positioning an indwelling heat exchange catheter in the carotid artery, heat can be removed from the brain to cool the brain and induce cerebral hypothermia. In this manner, temperature reduction can be confined to the brain, or other select body portion, while the remaining portions of the body maintain a generally normal body temperature. In accordance with this procedure, the selected body portion can be cooled to thereby provide the advantages associated with hypothermia for that body portion. The remainder of the body does not necessarily experience the reduction in temperature. Of course, selective cooling is application-dependent and it should be recognized that in some situations selective cooling may give way to systemic cooling in which the temperature of the whole body of the patient is cooled using a similar approach.

In addition to lowering body temperature, it may be advantageous to raise body temperature, either systemically or locally. An obvious situation in which raising body temperature systemically is desirable is following certain types of surgical procedure, for example after cardiopulmonary bypass surgery, to restore normothermic conditions after having cooled the patient in order to realize some of the aforementioned advantages of lowered body temperature. Another obvious example of the desirability of systemic warming of a patient is in emergency treatment of an accidentally hyperthermic patient.

U.S. Pat. No. 6,146,411 (Noda, et al.) teaches patient temperature control using an indwelling heat exchange catheter in thermal communication with a water bath. Thermal communication is achieved using a pair of closed fluid circuits each having a heat exchange fluid circulated therein. Pumps associated with each circuit control the circulation rate, and, consequently, the rate of heat exchange between the heat exchange catheter and the patient. The temperature of the water bath is adjusted in accordance with control signals issued to a chiller from a temperature controller. A probe provides a patient temperature reading to the controller, and a feedback loop arrangement is established whereby patient temperature control is effected by the temperature controller based on core body temperature readings from the probe. The controller operates to raise or lower body temperature and automatically maintain it at a target temperature or range, relying on heat transfer between the indwelling catheter and a selected portion of the body of the patient. When the target temperature is reached, heat transfer is stopped. A deviation from the target temperature or range, as measured by the probe, causes the controller to commence corrective measures, for instance lowering the temperature of the water bath if the core body temperature exhibits a rise. The controller also exerts temperature control by actively controlling the pumping rate of heat exchange fluid in one or both fluid circuits.

While the aforementioned prior art provides satisfactory control of patient body temperature, it has been found that response time may be inadequate in some situations. In a patient temperature control system using a circulation temperature controlled fluid as an intermediary medium for thermal energy transfer, conditions may arise wherein there is a temporary inversion of the source fluid temperature difference relative to the patient's blood temperature.

Consider the example of target temperature "undershoot," where the patient temperature drops below the target control temperature, while the bath (system control variable) is at or near its low temperature limit of 0° C. If the patient temperature trend is strongly negative (that is, a large dT/dt, signifying a rapid rate of patient cooling), it can be inferred that the system's available cooling power exceeds what is required to simply stably hold the patient at the target temperature. Should this occur, the normal system response is to raise the bath temperature, thereby reducing the saline-to-blood temperature difference ($\Delta T_{bb}$). The lower $\Delta T_{bb}$ reduces the cooling power of the catheter; by this method, the progressive action of a negative feedback control loop serves to stabilize the patient temperature.

However, the thermal mass of the bath and its attendant wetted components precludes instantaneous changes in bath temperature. Thus, while the bath temperature is being "slewed" from its "colder-than-required" state to its new intermediate state, the patient would continue to be cooled at a higher-than-desired rate. Since cooling power in excess of that required would continue to be applied to the patient's body during this bath temperature slew event, the body temperature would continue to decrease in response to the "excess" cooling until the bath assumed its new, desired higher level. The expected result is "undershoot," where the patient's temperature continues to drop below the target temperature until the overcooling condition is alleviated.

This extends the amount of time required to stabilize the temperature of the patient, thus protracting the surgical procedure and the length of time that the patient needs to be hooked up to the temperature control system. It may also pose a safety risk to the patient, overcooling or overheating the patient due to the system's delayed response.

BRIEF SUMMARY OF THE INVENTION

The above shortcomings of the prior art are addressed by a method for changing the temperature of the body of a patient using a thermal exchange device in accordance with the invention, wherein heat is transferred between the body of the patient and the thermal exchange device at a first heat transfer rate, the thermal exchange device is decoupled from the body of the patient, and heat is transferred between the body of the patient and the thermal exchange device at a second heat transfer rate.

Further in accordance with the invention, a method is described for changing the temperature of the body of a patient using a catheter in heat exchange relationship with a fluid bath, wherein a first fluid bath temperature is established, and heat is transferred between the fluid bath and the body of the patient. The fluid bath is decoupled from the body of the patient. A second fluid bath temperature is established, and heat is transferred between the fluid bath and the body of the patient.

Further in accordance with the invention, a system for changing the temperature of a patient using a catheter implanted in the patient includes a fluid bath, a fluid circuit adapted to contain a circulating heat exchange fluid in heat exchange relationship with the fluid bath and the catheter, a pump operable to circulate the heat exchange fluid in the fluid circuit, and a controller adapted to control the pump such that circulation of the heat exchange fluid in the fluid circuit is reduced to a vanishingly low level during a change in the temperature of the fluid bath between a first level and a second level when the catheter is implanted in the patient.

Further in accordance with the invention, a system for changing the temperature of a patient using a catheter implanted in the patient includes a thermal exchange device, a fluid circuit adapted to contain a circulating heat exchange fluid in heat exchange relationship with the thermal exchange device and the catheter, and a controller adapted to thermally decouple the catheter from the thermal exchange device during a change in the temperature of the thermal exchange device between a first level and a second level when the catheter is implanted in the patient.

Further in accordance with the invention, a system for changing the temperature of a patient using a catheter implanted in the patient includes heating and/or cooling means, means for transferring heat between the heating and/or cooling means and the catheter, and means for thermally decoupling the catheter from the heating and/or cooling means during a change in the temperature of the heating and/or cooling means between a first level and a second level when the catheter is implanted in the patient.

Further in accordance with the invention, a method for driving the temperature of the body of a patient to a predetermined target temperature or range using a thermal exchange device includes thermally coupling the thermal exchange device and the body of the patient when the temperature of the body of the patient is less than the predetermined target temperature or range and is less than the temperature of the thermal exchange device, or when the temperature of the body of the patient is greater than the predetermined target temperature or range and is greater than the temperature of the thermal exchange device; and thermally decoupling the thermal exchange device and the body of the patient when the temperature of the body of the patient is greater than the predetermined target temperature or range but is less than the temperature of the thermal exchange device, or when the temperature of the body of the patient is less than the predetermined target temperature or range but is greater than the temperature of the thermal exchange device.

BRIEF DESCRIPTION OF THE SEVERAL VIEWS OF THE DRAWING

Many advantages of the present invention will be apparent to those skilled in the art with a reading of this specification in conjunction with the attached drawings, wherein like reference numerals are applied to like elements and wherein.

DETAILED DESCRIPTION OF THE INVENTION

Figure 1:
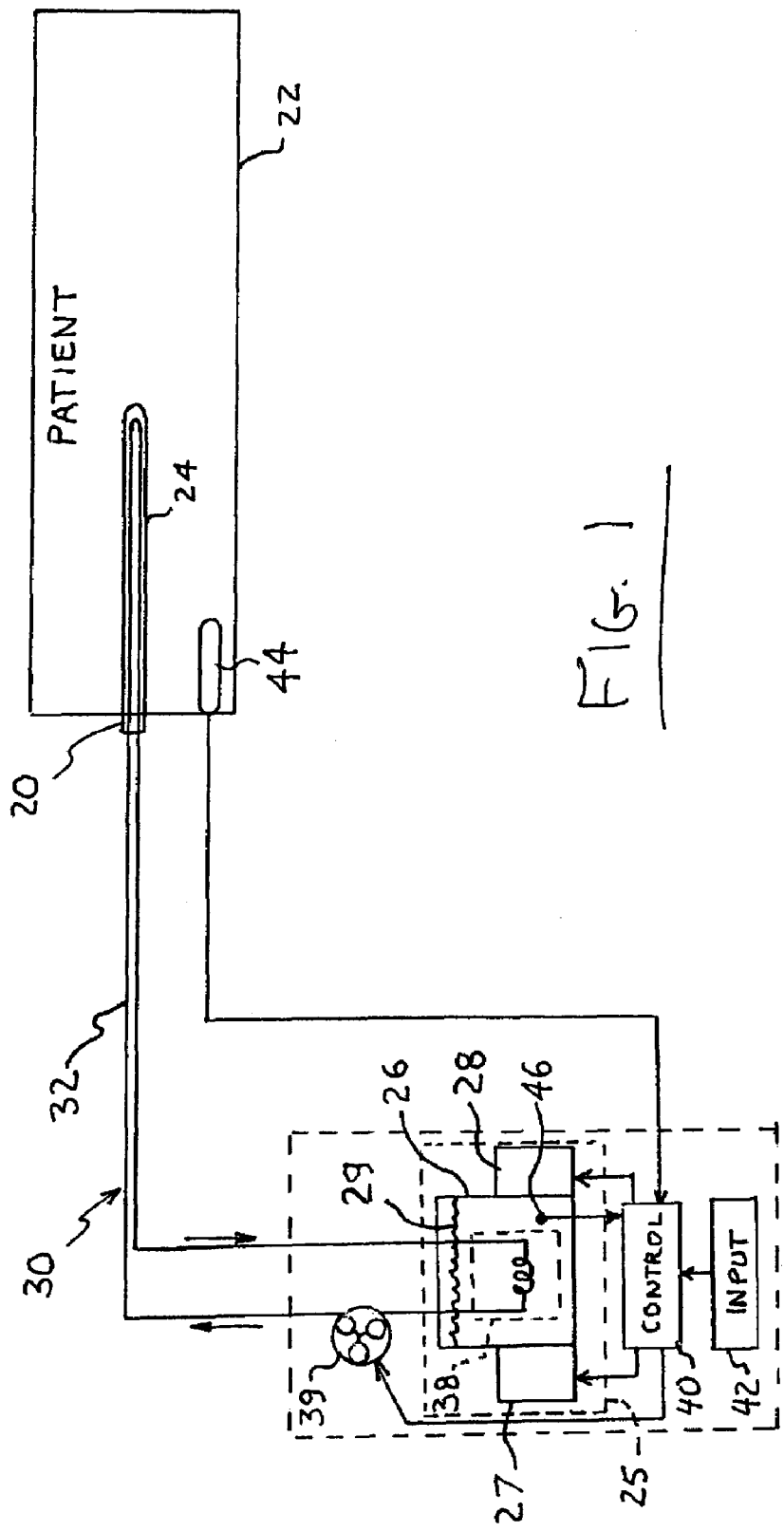
FIG. 1 is a schematic diagram showing operation of a system and method in accordance with the invention.

FIG. 1 schematically shows a system for patient temperature control operated in accordance with the invention. A catheter 20 is implanted in a patient 22 such that a heat exchange portion 24 of the catheter is in heat exchange relationship with a portion of the body of the patient, for example blood flowing past the heat exchange portion in a selected blood vessel (not shown). Heat exchange portion 24 is in thermal communication with a thermal exchange device 25, which includes a fluid bath 26, a heating device 27 and a cooling device 28. Heating and cooling devices 27 and 28 operate to selectively add heat to or remove heat from fluid bath 26, and in particular, fluid 29 thereof, as desired.

Thermal communication between thermal exchange device 25 and heat exchange portion 24 takes place directly or indirectly, via a heat exchange path indicated generally at 30. In the exemplary direct path approach illustrated, a single, closed fluid circuit 32 is used. Circuit 32 contains a circulating heat exchange fluid (not shown) in heat exchange relationship with fluid 29 in fluid bath 26, for example via heat exchanger 38. Fluid 29 is isolated from the heat exchange fluid in fluid circuit 32 in order to maintain sterility. Circulation in circuit 32 is motivated by a roller pump 39. Other types of pumps can be used, as will be appreciated. These include internal or external gear-type pumps, impeller pumps, vane pump, centrifugal pumps, piston pumps, diaphragm pumps, bladder pumps, gerotor pumps, peristaltic pumps, and the like. It will also be appreciated that more than one thermally coupled fluid circuit can be used, each having a pump associated therewith.

Heating device 27 and cooling device 28 of thermal exchange device 25 respectively operate to add heat to, and remove heat from, fluid bath 26, commensurately changing the temperature of the circulating heat exchange fluid in fluid circuit 32, heat exchange portion 24 of catheter 20, and, ultimately, patient 22. A temperature controller 40 provides control signals to thermal exchange device 25, and particularly, to devices 27 and 28, in order to selectively control the operation of devices 27 and 28 in accordance with a prescribed regimen. The control signals are issued as a function of several variables, including operator input and temperature feedback measurements from the patient 22 and water bath 26. An input device 42, for example a keypad, serves as an entry point for programming the prescribed regimen into controller 40, or for manually entering operation commands to the system. A temperature probe 44, such as a bladder or rectal catheter containing a thermistor device, provides patient temperature information to controller 40. A similar thermistor device 46 can be used to provide information pertaining to the temperature of fluid bath 26 and other components of the system. The temperature information from the patient is preferably core body temperature, although in a non-systemic approach the temperature of a particular portion of the body can be used.

Controller 40 uses the feedback from probe 44 to provide automatic patient temperature control. Such control can be in the form of warming the patient to a target temperature or range, cooling the patient to a target temperature or range, or cycling the patient between one or more target temperatures or ranges. The target temperatures or ranges can be above or below normal body temperature. Moreover, once a target temperate or range is achieved, the temperature or range can be maintained for any prescribed duration, then changed, and the new temperature or range maintained for another prescribed duration, and so on.

In accordance with the invention, the operation of pump 39 is controlled by controller 40 such that its pumping action is stopped during certain periods of system operation. Preferably, the roller pump is placed in "idle" mode, whereby it may continue to rotate at a rate sufficient to prevent damage or permanent deformation of the tubing against which it rolls, but not sufficient to effect any appreciable pumping of the fluid in this tubing. Cessation of pumping action in effect thermally decouples heat exchange portion 24 of catheter 20 from the remainder of the system, and in particular, from fluid bath 26. In this manner, fluid bath 26 can be ramped up, or "slewed", to a new temperature while disconnected from the patient, so that the delay in the system response does not undesirably affect the patient. The new temperature to which the fluid bath is slewed can be one which is beyond the target temperature or range, or it can be one which is not quite as far as the target or range. Thus, in one application, a first temperature at which the fluid bath is thermally coupled to the patient may be one which causes cooling of the patient (heat is transferred from the patient to the fluid bath). The second temperature, following thermal decoupling and slewing of the fluid bath, can be one which also causes cooling, but at a lower rate, or it can be one which causes heating of the patient (heat is transferred from the fluid bath to the patient). Conversely, in another application, the first temperature can cause heating of the patient, and the second temperature following thermal decoupling and slewing, can cause heating at a lower rate, or can cause cooling. It will be appreciated that any such combination of heating or cooling can be applied depending on the desired regimen as programmed into the system or effected manually.

Figure 2:
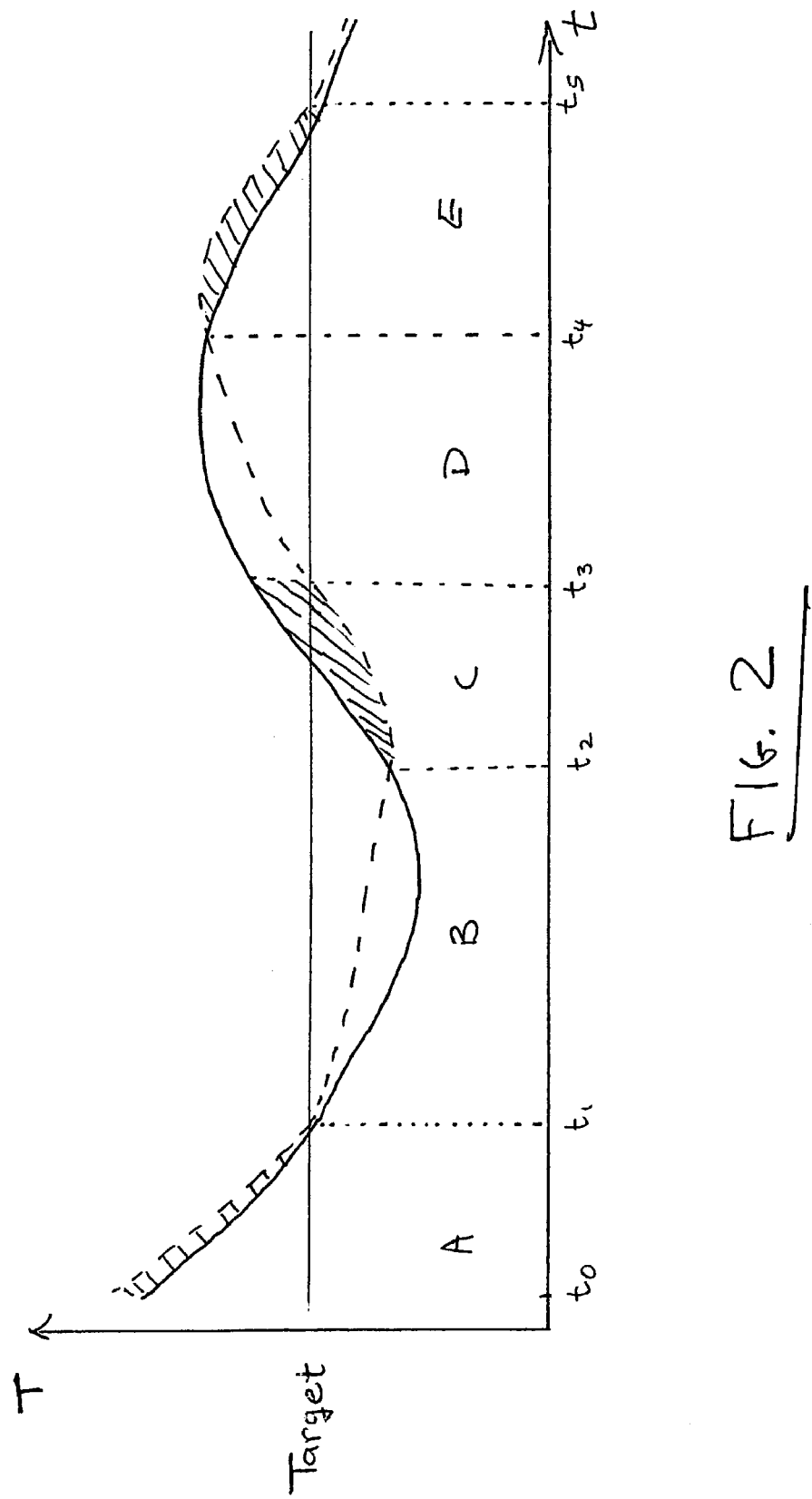
FIG. 2 is a graphic representation of temperature control in accordance with the invention.

FIG. 2 is a plot characterizing the operation of the system in accordance with the invention, wherein the dashed curve represents the patient and the solid curve represents the temperature of the fluid bath. Initially, at a time $t_0$, the temperature of the patient is above target temperature, for example 37° C. Thus cooling is applied to the patient, during Period A, by cooling fluid bath 26 and circulating heat exchange fluid between the fluid bath and the implanted catheter 20. When, at $t_1$, the patient temperature reaches the target temperature or a vicinity thereof, catheter 20 is decoupled from the fluid bath 26, so that while the temperature of fluid bath 26 drops at a relatively steep rate due to its thermal mass, the temperature of the patient, if it continues to drop at all, will not do so at the same steep rate. During the decoupling (Period B), the water bath is slewed to a new, intermediate temperature, by being warmed using heater 27. Then, when at time $t_2$ the intermediate temperature is reached, water bath 26 and catheter 20 are thermally re-coupled—that is, pump 39 is turned on again by controller 40, and the system begins pulling the temperature of the patient back up, towards the target (Period C). At time $t_3$, patient temperature again reaches the target, and water bath 26 and catheter 20 are again thermally decoupled by turning pump 39 off. The water bath is slewed to a new, intermediate temperature in Period D, and when that intermediate temperature is reached at time $t_4$, re-coupling is effected such that the system pulls patient temperature back down towards target (Period E), which is reached at $t_5$, and so on.

It will be noted from the above that coupling most desirably takes place when the temperature of the body of the patient is less than the target temperature or range and is less than the water bath temperature (Period C), or when temperature of the body of the patient is greater than the target temperature or range and greater than the water bath temperature (Periods A and E). Conversely, decoupling is most desirable when the temperature of the body of the patient is greater than the target temperature or range but is less than water bath temperature (Period D), or when the temperature of the body is less than target temperature or range but is greater than water bath temperature (Period B).

It will further be appreciated that for ease of description, the above discussion referred to specific coupling and decoupling times and events. In practice, the coupling and decoupling times and events may have to be triggered earlier or later than the times alluded to, for instance in order to account for the thermal mass of the system and anticipate its effects. In such a case, thermal coupling and decoupling may more properly be performed in advance of the times $t_1$, $t_2$, etc. Those of ordinary skill in the art will appreciate that variations to the methods and systems described can be made in accordance with the particular application, and the operating algorithms can be selected for optimal performance for such application, without departing from the spirit and scope of the invention as set forth in the following claims.

The invention claimed is:

1. A method for changing the temperature of the body of a patient using a thermal exchange device comprising:
   transferring heat between the body of the patient and the thermal exchange device at a first heat transfer rate by implanting a catheter into the body of the patient and circulating a heat exchange fluid with a pump in a heat exchange relationship between the catheter and a fluid bath;
   stopping the pump when a target temperature is reached and leaving the catheter in the patient;
   slewing the fluid bath;
   restarting the pump; and
   transferring heat between the body of the patient and the thermal exchange device at a second heat transfer rate.

2. The method of claim 1, wherein stopping the pump when a target temperature is reached and leaving the catheter in the patient comprises reducing the circulation rate of the heat exchange fluid to a vanishingly low level.

3. The method of claim 2, further comprising:
   determining the temperature of the patient relative to a predetermined range;
   determining the temperature of the thermal exchange device; and wherein stopping the pump when a target temperature is reached and leaving the catheter in the patient is performed when the temperature of the body of the patient is greater than the predetermined range but is less than the temperature of the thermal exchange device.

4. The method of claim 2, further comprising:
determining the temperature of the patient relative to a predetermined range;
determining the temperature of the thermal exchange device; and
stopping the pump when a target temperature is reached and leaving the catheter in the patient is performed when the temperature of the body of the patient is less than the predetermined range and is less than the temperature of the thermal exchange device.

5. The method of claim 2, further comprising:
determining the temperature of the patient relative to a predetermined target temperature; and
determining the temperature of the thermal exchange device, wherein reducing the circulation of heat exchange fluid is performed when the temperature of the body of the patient is greater than the predetermined target temperature but is less than the temperature of the thermal exchange device.

6. The method of claim 2, further comprising:
determining the temperature of the patient relative to a predetermined target temperature; and
determining the temperature of the thermal exchange device, wherein reducing the circulation of heat exchange fluid is performed when the temperature of the body of the patient is less than the predetermined target temperature but is greater than the temperature of the thermal exchange device.

7. The method of claim 2, further comprising:
determining the temperature of the patient relative to a predetermined range; and
determining the temperature of the thermal exchange device, wherein reducing the circulation of heat exchange fluid is performed when the temperature of the body of the patient is less than the predetermined range but is greater than the temperature of the thermal exchange device.

8. The method of claim 2, further comprising:
determining the temperature of the patient relative to a predetermined range;
determining the temperature of the thermal exchange device; and
reducing the circulation of heat exchange fluid the thermal exchange device and the body of the patient when the temperature of the body of the patient is greater than the predetermined range and is greater than the temperature of the thermal exchange device.

9. The method of claim 1, wherein the first heat transfer rate is one of cooling or heating the body of the patient, and the second heat transfer rate is the other of cooling or heating the body of the patient.

10. The method of claim 1, wherein both the first and second heat transfer rates comprise cooling the body of the patient.

11. The method of claim 1, wherein the thermal device comprises:
the heat exchange fluid bath;
the fluid circuit adapted to contain the circulating heat exchange fluid in heat exchange relationship with the fluid bath and the catheter;
the pump operable to circulate the heat exchange fluid in the fluid circuit; and
a controller adapted to control the pump, wherein the circulation of the heat exchange fluid in the fluid circuit stops circulating between the fluid bath and the patient during a change in the temperature of the fluid bath between a first level and a second level when the catheter is implanted in the patient.

12. The method of claim 1, wherein both the first and second heat transfer rates comprise heating the body of the patient.

13. A method for changing the temperature of the body of a patient using a catheter in heat exchange relationship with a fluid bath, the method comprising:
establishing a first fluid bath temperature;
when the fluid bath is at the first fluid bath temperature, transferring heat between the fluid bath and the body of the patient by circulating a heat exchange fluid in heat exchange relationship with the catheter and the fluid bath;
stopping the circulation of fluid when a target temperature is reached and leaving the catheter in the patient;
establishing a second fluid bath temperature; and
when the fluid bath is at the second fluid bath temperature, restarting the circulation of fluid and transferring heat between the fluid bath and the body of the patient.

14. The method of claim 13, wherein is performed when the temperature of the body of the patient is greater than a predetermined range but is less than the temperature of the fluid bath.

15. The method of claim 13, further comprising reducing the circulation rate of the heat exchange fluid to a vanishingly low level.

16. The method of claim 13, further comprising stopping the circulation of fluid when a target temperature is reached and leaving the catheter in the patient when the temperature of the body of the patient is less than a predetermined range and is less than the temperature of the fluid bath.

17. The method of claim 13, wherein the direction of heat transfer is the same at both the first and second fluid bath temperatures.

18. The method of claim 13, wherein the direction of heat transfer at the first fluid bath temperature is different from the direction of heat transfer at the second fluid bath temperature.

19. The method of claim 13, wherein stopping the pump when a target temperature is reached and leaving the catheter in the patient is performed when the temperature of the body of the patient is less than a predetermined range but is greater than the temperature of the fluid bath.

20. The method of claim 13, further comprising a pump operable to circulate the heat exchange fluid in the fluid circuit and stopping the circulation of the heat exchange fluid by stopping the pump when a target temperature is reached and leaving the catheter in the patient is performed when the temperature of the body of the patient is greater than a predetermined range and is greater than the temperature of the fluid bath.

21. The method of claim 13, further comprising a pump operable to circulate the heat exchange fluid in the fluid circuit.

22. The method of claim 21, further comprising stopping the circulation of the heat exchange fluid by stopping the pump.

23. A method for changing the temperature of the body of a patient comprising:
implanting a catheter into the body of the patient;

circulating a heat exchange fluid in heat exchange relationship between the patient and a fluid bath at a first transfer rate;

stopping the circulation of the heat exchange fluid between the patient and the fluid bath when a target temperature is reached and leaving the catheter in the patient;

slewing the fluid bath;

restarting the circulation of the heat exchange fluid; and circulating the heat exchange fluid between the catheter and the fluid bath at a second transfer rate.

24. The method of claim 23, further comprising a pump operable for stopping the circulation of the heat exchange fluid when the target temperature is reached.

\* \* \* \* \*